United States Patent [19]

Maulding

[11] 4,076,728
[45] Feb. 28, 1978

[54] PROCESS FOR MANUFACTURING CRYSTAL VIOLET LACTONE

[75] Inventor: Donald Roy Maulding, Somerville, N.J.

[73] Assignee: American Cyanamid Company, Stamford, Conn.

[21] Appl. No.: 778,399

[22] Filed: Mar. 17, 1977

[51] Int. Cl.² ............................................. C07D 307/88
[52] U.S. Cl. .................................. 260/343.4; 260/391
[58] Field of Search ............................... 260/343.4, 391

[56] References Cited

U.S. PATENT DOCUMENTS

| Re. 23,024 | 8/1948 | Adams | 260/343.4 |
|---|---|---|---|
| 2,742,483 | 4/1956 | Crounse | 260/343.4 |
| 3,842,103 | 10/1974 | Smith | 260/391 |
| 3,845,077 | 10/1974 | Hughes | 260/343.4 |
| 3,987,062 | 10/1976 | Okada et al. | 260/343.4 |

FOREIGN PATENT DOCUMENTS 1,962,881  7/1971  Germany ........................... 260/343.4

Primary Examiner—Norma S. Milestone
Attorney, Agent, or Firm—John L. Sullivan

[57] ABSTRACT

Crystal Violet Lactone (CVL) is produced in high yield and highly pure form by a process comprising condensing Michlers hydrol with 3-dimethylaminobenzoic acid to form leuco CVL, extracting the reaction mixture containing the leuco CVL with an aromatic hydrocarbon solvent, such as toluene, or a mixture of such a solvent and a water-immiscible alkane, such as heptane, to remove impurities therefrom and treating the extracted reaction mixture with an inorganic oxidizing agent to convert the leuco CVL to CVL.

8 Claims, No Drawings

PROCESS FOR MANUFACTURING CRYSTAL VIOLET LACTONE

This invention relates to a process for the manufacture of Crystal Violet Lactone (CVL), chemically identified as 3,3-bis(4-dimethylaminephenyl)-6-dimethylaminophthalide, represented by the structure:

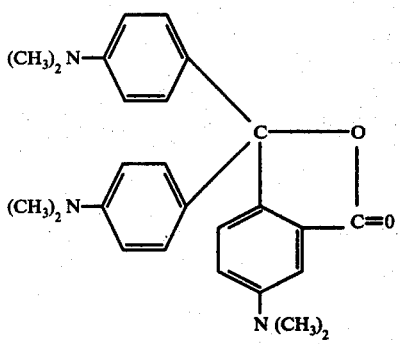

In particular, the invention relates to an improved process for the preparation of Crystal Violet Lactone in high yield and purity.

Crystal Violet Lactone is a well-known compound used in paper coating compositions for the manufacture of carbonless carbon paper. The compound, and its precursor leuco Crystal Violet Lactone (LCVL), chemically identified as 2-[4,4'-bis(dimethylamino)benzhydryl]-5-dimethylaminobenzoic acid, having the structure:

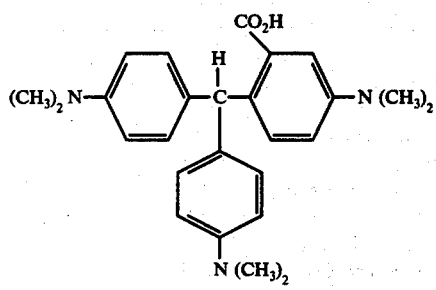

are well-known (Adams, U.S. Pat. Nos. 2,417,897 and 2,458,328).

Conventionally, tetramethyl-4,4'-diaminobenzhydrol (Michlers hydrol),

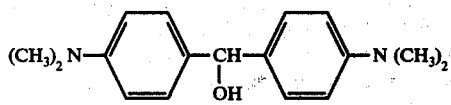

is condensed with 3-dimethylaminobenzoic acid,

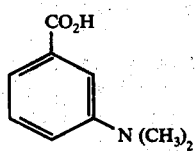

under acidic conditions to form leuco Crystal Violet Lactone, which is then oxidized to Crystal Violet Lactone.

The condensation of Michlers hydrol with 3-dimethylaminobenzoic acid under acidic conditions, i.e., in acidic medium, is known (Adams, supra, and Smith et al. U.S. Pat. No. 3,842,103). Since it has been generally conceded that the yield and purity of Crystal Violet Lactone are dependent on the purity of its precursor leuco Crystal Violet Lactone, it has been common practice to isolate the leuco compound and to purify it before proceeding to the oxidation step. While it is possible to obtain pure product in this manner, the overall yield is low due to losses resulting from the isolation and purification procedures. On the other hand, if the leuco compound is not isolated and purified before oxidation the product is obtained impure and in low yield and must be purified.

None of the prior methods have succeeded in preparing Crystal Violet Lactone in good yields of pure product without isolation and purification of the leuco precursor. It is the principal object of the present invention to provide such a process.

The process of the invention is based on the discovery that leuco Crystal Violet Lactone may be purified in situ before oxidation, by extraction of the reaction mixture with an aromatic solvent, such as toluene, or a mixture of such a solvent and suitable water-immiscible alkane.

The process has the advantage that the leuco compound is not isolated from the reaction mixture, is purified therein and may then be oxidized to Crystal Violet Lactone having a suitable high purity without recrystallization. Accordingly, the process is more economical than those previously available.

The condensation reaction of one mole proportion of Michlers hydrol with from about 0.9-1.2 mole proportions of 3-dimethylaminobenzoic acid is conducted according to known procedures by heating the reaction mixture at 65°-100° C., preferably 90°-100° C., in 20% sulfuric acid. The reaction mixture is then cooled down to about 50°-60° C., made alkaline by the addition of base, e.g., sodium hydroxide, to convert the leuco compound into its sodium salt. The aqueous alkaline solution is then extracted at a temperature of 40°-90° C., preferably 50°-60° C., with toluene, or a mixture of toluene and a suitable water-immiscible alkane.

It has been found that the major impurity extracted from the leuco Crystal Violet Lactone reaction mixture is leuco Crystal Violet (LCV) having the structure:

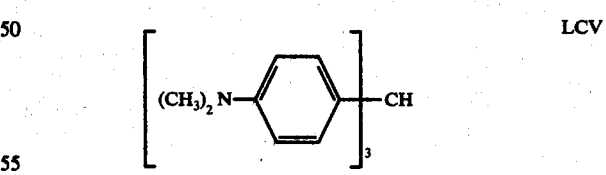

Toluene has been found to be a good extractant for the reaction product. However, toluene is not readily completely removed from the reaction mixture following extraction and, therefore, unless care is taken to remove it, some Crystal Violet Lactone, when formed, is lost due to solubility in the toluene remaining in the reaction mixture. For this reason, it is preferable to conduct the extraction using a mixture of toluene and a suitable water-immiscible liquid alkane, e.g., heptane or VM & P Naphtha (primarily cycloparaffins, e.g., cyclopentane and cyclohexane). Equal weight mixtures of toluene and heptane or toluene and VM & P Naphtha were found to be excellent extractants. In addition, very good phase separations result, so that essentially none of the organic extractant remains in the reaction mixture following the extraction. Small yield losses of Crystal Violet Lactone are thereby avoided.

Although the process is exemplified herein with reference to toluene and mixtures of toluene and heptane or VM & P Naphtha, other aromatics, e.g. xylene, and other alkanes and combinations thereof may be useful provided (1) they are water-immiscible, (2) provide clean separations from the aqueous alkaline reaction mixture, (3) dissolve the impurities and (4) do not dissolve the sodium salt of leuco Crystal Violet Lactone.

The amount of extractant used is not critical so long as sufficient amount is used to remove the impurities present in the leuco Crystal Violet Lactone reaction mixture. In general, for a single stage extraction about 1000 to 4000 parts by weight of extractant are used per mole proportion of Michlers hydrol used in the condensation reaction. Multiple stage extractions would significantly reduce this quantity.

Following extraction the aqueous alkaline solution of leuco Crystal Violet Lactone is oxidized according to known procedures. Many oxidants may be used, including hydrogen peroxide, potassium permanganate and inorganic persulfates. In the present invention we prefer to use an inorganic persulfate oxidant (Hughes, U.S. Pat. No. 3,842,103), particularly potassium persulfate. Preferably about 1.1-1.2 moles of potassium persulfate are used per mole of Michlers hydrol used in the condensation reaction, at a temperature of about 55°-65° C.

The following examples will serve to illustrate the invention.

EXAMPLE 1

(A) A well-stirred vessel is charged with 742 parts by weight of water to which is added 230.3 parts by weight of 100% sulfuric acid (4.7 equivalents). When all the acid is added 181.5 parts by weight (1.1 mole proportion) of 3-di-methylaminobenzoic acid is added to the warm solution. The vessel is purged with nitrogen and 270 parts by weight (0.96 mole proportion of tetrametryl-4,4'-diaminobenzhydrol is added. The reaction mixture is heated to 90°-95° C. and held for about 2 hours under nitrogen.

(B) A second vessel is charged with 9510 parts by weight of water to which is added 672 parts by weight of sodium hydroxide. To this solution is added the condensation product from Part A and the contents heated to 50°-55° C. Toluene (1730 parts by weight) and VM & P Naphtha (1730 parts by weight) are added and the contents stirred for about 15 minutes at 50°-55° C. The aqueous phase is allowed to separate from the organic phase and the aqueous phase is withdrawn to a third (oxidation) vessel.

(C) The extracted aqueous solution is heated to 50°-55° C. and stirred. To this solution is added 12 parts by weight of toluene and then a solution of 2893 parts by weight of water and 307.8 parts by weight of potassium persulfate at 60° C. is added over a period of 15-20 minutes with cooling to maintain the temperature in the range 55°-65° C. Following addition of all the oxidant the reaction mixture is stirred for an additional 15 minutes at 55°-65° C. and then cooled to 50° C. A major portion of the mother liquor is decanted from the solids which precipitate on cooling and the resulting slurry is centrifuged, washed with 973 parts by weight of a 2.5% solution of sodium hydroxide, then with water. The centrifuge cake is discharged and dried at 80°-130° C. The yield is 266 parts by weight of Crystal Violet Lactone (64%), m.p. 175°-180° C. (90% pure).

Similar results are obtained when heptane is used in place of VM & P Naphtha in the foregoing example.

EXAMPLE 2

To 11.6 grams of concentrated sulfuric acid in 48 ml. of water was added 9.07 grams (0.055 mole) of 3-dimethylaminobenzoic acid. To the resulting solution was added 13.5 grams (0.05 mole) of tetrametryl-4,4'-diaminobenzhydrol and the mixture was heated with stirring at 95° C. for 2 hours. The solution was cooled to 50°-60° C. and added in portions to a solution of 16.7 grams of sodium hydroxide in 390 ml. of water. The resulting solution was warmed to 55°-65° C. and extracted with 80 ml. of toluene. The aqueous solution at 55° C. was then treated with a solution of 14.9 grams (0.055 mole) of potassium persulfate in 140 ml. of water over a period of 15 minutes and the reaction mixture stirred an additional 15 minutes at 65° C. The product was filtered and washed with water. There was obtained 62% yield of a product having a purity of 98%, m.p. 180°-183° C.

I claim:

1. A process for preparing 3,3-bis(4-dimethylaminophenyl)-6-dimethylaminophthalide which comprises reacting one mole proportion of tetramethyl-4,4'-diaminobenzhydrol with from about 0.9 to about 1.2 mole proportions of 3-dimethylaminobenzoic acid in aqueous sulfuric acid at a temperature of 65°-100° C. to form 2-[4,4'-bis(dimethylamino)benzhydryl]-5-dimethylaminobenzoic acid, adding sodium hydroxide to the reaction mixture to form the sodium salt of the said benzoic acid therein, contacting the reaction mixture at a temperature of about 40°-90° C. with a solvent selected from a liquid aromatic hydrocarbon and a mixture of liquid aromatic hydrocarbon and a water-immiscible alkane, whereby impurities present in said solution are extracted therefrom; separating the organic extract phase from the aqueous reaction mixture phase, treating the reaction mixture phase with an inorganic oxidizing agent to oxidize the sodium salt of the 2-[4,4'-bis(dimethylamino)benzhydryl]-5-dimethylaminobenzoic acid to the 3,3-bis-(4-dimethylaminophenyl)-6-dimethylaminophthalide product and recovering said product from the reaction mixture.

2. A process according to claim 1 wherein the solvent is toluene.

3. A process according to claim 1 wherein the solvent is a mixture of toluene and heptane.

4. A process according to claim 1 wherein the solvent is a mixture of toluene and a naphtha consisting essentially of cyclopentane and cylohexane.

5. A process according to claim 1 wherein the oxidizing agent is potassium persulfate.

6. A process according to claim 1 wherein the oxidizing agent is hydrogen peroxide.

7. A process according to claim 2 wherein the oxidizing agent is potassium persulfate.

8. A process according to claim 4 wherein the oxidizing agent is potassium persulfate.

* * * * *